(12) United States Patent
Therriault et al.

(10) Patent No.: US 6,174,546 B1
(45) Date of Patent: *Jan. 16, 2001

(54) TRANSDERMAL PRESSURE SENSITIVE ADHESIVE DRUG DELIVERY SYSTEM

(75) Inventors: Donald J. Therriault; Michael J. Zajaczkowski, both of York; Barbara A. Stutzman, Dover, all of PA (US)

(73) Assignee: Adhesives Research, Inc., Glen Rock, PA (US)

( * ) Notice: Under 35 U.S.C. 154(b), the term of this patent shall be extended for 0 days.

This patent is subject to a terminal disclaimer.

(21) Appl. No.: 09/562,450

(22) Filed: May 1, 2000

Related U.S. Application Data

(63) Continuation of application No. 09/255,271, filed on Feb. 23, 1999, now abandoned, which is a continuation of application No. 08/803,594, filed on Feb. 21, 1997, now Pat. No. 5,951,999.

(51) Int. Cl.[7] .................................................... A61F 13/02
(52) U.S. Cl. ............................................. 424/448; 424/449
(58) Field of Search ..................................... 424/448, 449

(56) References Cited

U.S. PATENT DOCUMENTS

| | | |
|---|---|---|
| 3,786,116 | 1/1974 | Milkovich et al. . |
| 3,832,423 | 8/1974 | Milkovich et al. . |
| 3,842,057 | 10/1974 | Milkovich et al. . |
| 3,842,058 | 10/1974 | Milkovich et al. . |
| 3,842,059 | 10/1974 | Milkovich et al. . |
| 3,842,146 | 10/1974 | Milkovich et al. . |
| 3,862,098 | 1/1975 | Milkovich et al. . |
| 3,862,101 | 1/1975 | Milkovich et al. . |
| 3,862,102 | 1/1975 | Milkovich et al. . |
| 4,554,324 | 11/1985 | Husman et al. . |
| 5,108,995 | 4/1992 | Casper . |
| 5,223,261 | 6/1993 | Nelson et al. . |
| 5,242,951 | 9/1993 | Akemi et al. . |
| 5,352,516 | 10/1994 | Therriault et al. . |
| 5,422,119 | 6/1995 | Casper . |
| 5,460,820 | 10/1995 | Ebert et al. . |
| 5,573,778 | 11/1996 | Therriault et al. . |

FOREIGN PATENT DOCUMENTS

| | | |
|---|---|---|
| 728780 | 8/1996 | (EP) . |
| 95/14746 | 6/1995 | (WO) . |
| 96/08229 | 3/1996 | (WO) . |

*Primary Examiner*—Thurman K. Page
*Assistant Examiner*—Brian K. Seidleck

(57) ABSTRACT

A transdermal drug delivery system is provided which includes an optionally crosslinked macromer-reinforced (meth)acrylic ester base copolymer pressure sensitive adhesive wherein the macromer includes repeat hydrophilic units.

116 Claims, No Drawings

TRANSDERMAL PRESSURE SENSITIVE ADHESIVE DRUG DELIVERY SYSTEM

CROSS-REFERENCE TO RELATED APPLICATION

This application is a continuation application of application Ser. No. 09/255,271, filed Feb. 23, 1999 now abandoned which is a continuation of application Ser. No. 08/803,594, filed Feb. 21, 1997, now U.S. Pat. No. 5,951,199.

BACKGROUND OF THE PRESENT INVENTION

The present invention is directed to a pressure sensitive adhesive useful in transdermal administration of pharmacologically active agents, in particular estrogen and/or progestin active agents.

The transdermal delivery of therapeutic agents has been the subject of intense research and development for over 20 years. These efforts have resulted in the creation of several commercially successful products whose advantages over other dosage forms are well documented. The skin, however, is an exceptionally well designed barrier. As a result, only a relatively small number of drug molecules are suitable for transdermal delivery, including hormones such as estrogen and/or progestin.

It is known to administer steroidal hormones such as estrogen and/or progestin active agents by transdermal means to a patient. See, for example, U.S. Pat. Nos. 5,108,995; 5,223,261; 5,242,951; 5,422,119; 5,460,820; and WO 96/08229. It has been found that such active agents are susceptible to crystallization within the adhesive matrix over time. Such crystallization inhibits the ability of the transdermal device to deliver the active agent to the patient.

The prior art does not provide a transdermal pressure sensitive adhesive which both serves as a satisfactory matrix for the delivery of an estrogen and/or progestin active agent as well as inhibiting the crystallization of such active agent in order to enhance the long-term effectiveness of the delivery system.

OBJECTS AND SUMMARY OF THE INVENTION

It is therefore an object of the present invention to provide a pressure sensitive adhesive drug delivery system which possesses acceptable compatibility with active drug agents while maintaining the appropriate viscoelastic characteristics for adequate skin adhesion.

It is also an object of the present invention to provide a pressure sensitive adhesive drug delivery system which reduces the tendency of hormones to crystallize within the transdermal drug delivery system.

In accordance with the present invention, there is thus provided a transdermal drug delivery composition having pressure sensitive adhesive properties comprised of (1) a graft copolymer comprised of a (meth)acrylic ester backbone copolymer optionally including at least one N-vinyl lactam monomer and having an optionally crooslinked polymeric moiety grafted thereto containing hydrophilic repeat units, and (2) a pharmacologically active agent in homogeneous admixture with said macromer reinforced base polymer.

In accordance with the present invention, there is also provided a transdermal drug delivery system for administering a pharmacologically active agent comprising a flexible backing material impermeable to said pharmacologically active agent and an adhesive layer on at least a portion of said backing material, the improvement wherein said adhesive layer comprises an optionally crosslinked graft copolymer comprised of a (meth)acrylic ester backbone copolymer optionally including at least one N-vinyl lactam monomer and having a polymeric moiety grafted thereto containing hydrophilic repeat units.

DETAILED DESCRIPTION OF THE INVENTION

The present invention is directed to a pressure sensitive adhesive transdermal drug delivery composition comprised of a graft copolymer as well as a transdermal delivery device utilizing such a composition.

The graft copolymer pressure sensitive adhesive employed in the present invention is comprised of a backbone polymer having a polymeric moiety grafted thereto. The graft copolymer comprises the reaction product of at least one (meth)acrylic acid ester A monomer (as defined), at least optional B monomer, optionally a polymeric graft moiety C having a $T_g$ greater than 20° C., and a polymeric graft moiety D containing hydrophilic repeat units.

The graft copolymer includes at least one A monomer consisting of a monomeric (meth)acrylic acid ester of a non-tertiary alcohol where the alcohol portion has from 1 to 30 carbon atoms. Exemplary A monomers include but are not limited to esters of acrylic acid or methacrylic acid with non-tertiary alcohols such as 1-butanol, 1-pentanol, 2-pentanol, 3-pentanol, 2-methyl-1-butanol, 1-methyl-1-pentanol, 2-methyl-1-pentanol, 3-methyl-1-pentanol, 2-ethyl-1-butanol, 3,5,5-trimethyl-1-hexanol, 3-heptanol, 2-octanol, 1-decanol, 1-dodecanol, etc.

Advantageously, it has been found useful to employ at least one A monomer formed from an alcohol having at least 12 carbon atoms. The use of an A monomer formed from an alcohol having at least 18 carbon atoms is particularly desirable. Such exemplary A monomers include but are not limited to lauryl acrylate ($C_{12}$), tridecylacrylate ($C_{13}$), myristyl acrylate ($C_{14}$), palmityl acrylate ($C_{16}$), and stearyl acrylate ($C_{18}$). Such monomers are known to those skilled in the art.

The presence of an A monomer having a carbon chain of at least 12 carbon atoms has been found to enhance the compatibility of the adhesive with oily or non-water soluble drug flux or skin permeation enhancers which may be employed. Such enhancers have not been found to be particularly compatible with conventional transdermal adhesives containing a major portion of A monomers formed from alcohols having from 4 to 12 carbon atoms. While the use of A monomers formed from alcohols having from 4 to 12 carbon atoms in the adhesive of the present invention is appropriate, it is preferable for the at least one A monomer component to comprise at least 30 percent by weight of an A monomer formed from an alcohol having greater than 12 carbon atoms. The at least one A monomer component (if more than one A monomer is present) will exhibit an average number of carbon atoms in the alcohol portion of the total acrylic or (meth)acrylic acid esters of from 4 to 16, and preferably at least 10.

One or more optional polymerizable B monomers may be incorporated in the copolymer which B monomer(s) is copolymerizable with the A monomer. Such additional B monomer(s) may be either hydrophilic or hydrophobic.

Exemplary optional B monomers include vinyl monomers having at least one nitrogen atom. Such monomers (each of which exhibit a $T_g$ of <20° C.) include but are not limited to N-mono-substituted acrylamides such as acrylamide, methacrylamide, N-methylacrylamide, N-ethylacrylamide, N-methylolacrylamide, N-hydroxyethylacrylamide, and diacetone acrylamide; N,N-disubstituted acrylamides such as N,N-dimethylacrylamide, N,N-diethylacrylamide, N-ethyl-N-aminoethylacrylamide, N-ethyl-N-hydroxyethylacrylamide, N,N-dimethylolacrylamide, and N,N-dihydroxyethylacrylamide, etc.

Other optional B monomers may include, for example, various vinyl monomers such as acrylic and methacrylic acid, methoxyethyl acrylate, or methacrylate, ethyoxyethyl acrylate or methacrylate, glycerol acrylate or methacrylate, hydroxyethyl methacrylate, hydroxypropyl methacrylate, beta-carboxyethyl acrylate, vinyl pyrrolidone and vinyl caprolactam (each of which also exhibit a $T_g$ of <20° C.).

The at least one B monomer preferably comprises an N-vinyl lactam monomer. Exemplary N-vinyl lactam monomers include but are not limited to N-vinyl-2-pyrrolidone; 5-methyl-N-vinyl-2-pyrrolidone; 5-ethyl-N-vinyl-2-pyrrolidone; 3,3-dimethyl-N-vinyl-2-pyrrolidone; 3-methyl-N-vinyl-2-pyrrolidone; 3-ethyl-N-vinyl-2-pyrrolidone; 4-methol-N-vinyl-2-pyrrolidone; 4-ethyl-N-vinyl-2-pyrrolidone; N-vinyl-2-valerolactam; N-vinyl-2-caprolactam; and mixtures of any of the foregoing. Preferably, the N-vinyl lactam is N-vinyl-2-pyrrolidone.

The optional graft polymeric moiety C has a $T_g$ greater than 20° C. Graft polymeric moiety C has the formula X—Z wherein X is a group copolymerizable with monomers A and B or capable of attachment to copolymerized A and B monomers and Z is a polymeric graft moiety having a $T_g$ greater than 20° C. The Z moiety is essentially unreactive under copolymerization conditions.

More specifically, the X moiety is an unsaturated polymerizable moiety the composition of which is not critical. The X moiety may be, for example, when intended to be copolymerizable with monomers A and B, simply a vinyl group of the formula CHR=CR¹— where R is hydrogen or COOH and R¹ is hydrogen or alkyl such as methyl. Other exemplary X moieties include but are not limited to methacryloyl, maleoyl, itaconoyl, crotonoyl, unsaturated urethane moiety, methacrylamido and moieties of the formula CH₂=CHCH₂O—.

The X moiety may comprise an amine or alcohol moiety (such as a monohydroxyl or monoamine moiety) which permits attachment of the macromer to a suitable functionality on previously-polymerized monomers A and B. For instance, the hydroxyl moiety can serve as a terminal reactive group by reaction with suitable moieties on the polymer backbone resulting from the use of monomers such as isocyanate-substituted (meth)acrylic acid, (meth)acrylic acid anhydride, etc.

A variety of functional groups may be employed to attach the graft Z to the polymer backbone.

Exemplary functional groups include but are not limited to

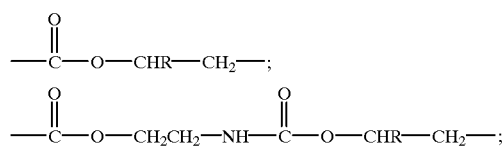

CH₂—O—CHR—CH₂—;

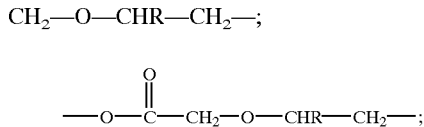

and —OCH₂CH₂—O—CHR—CH₂, where R is a hydrogen atom or a lower alkyl group.

With regard to the optional polymeric graft moiety C portion of the adhesive composition, U.S. Pat. Nos. 3,786,116; 3,842,057; 3,842,058; 3,842,059; 3,862,098; 3,862,101, 3,862,102 and 4,554,324 disclose polymerizable macromers which are suitable for use as graft moieties on a backbone polymer as defined.

Preferably, the polymeric moiety C is formed from a vinyl aromatic monomer such as styrene, alpha-methylstyrene, indene and p-tert-butylstyrene. However, the polymeric moiety Z may also be formed from vinyl toluene, acenaphthalene, acrylonitrile and methacrylonitrile; organic isocyanates including lower alkyl, phenyl, lower alkyl phenyl and halophenyl isocyanates; organic diisocyanates including lower alkylene, phenylene, and tolylene diisocyanates; lower alkyl and allyl acrylates and methacrylates, including methyl, t-butyl acrylates, and methacrylates; lower olefins, such as ethylene, propylene, butylene, isobutylene, pentene, hexene, etc.; vinyl esters of aliphatic carboxylic acids such as vinyl acetate, vinyl propionate, vinyloctoate, vinyl oleate, vinyl stearate, vinyl benzoate, vinyl lower alkyl ethers; conjugated dienes such as isoprene and butadiene; 2-oxazolines such as 2-ethyl-2-oxazoline; and vinyl unsaturated amides such as acrylamide, methylacrylamide, N,N-di(lower alkyl)acrylamides such as N,N-dimethylacrylamide.

The selection of the specific polymerizable monomer for the polymer graft is not critical, since as the above listing suggests, a wide variety of monomers (and the resulting polymeric moieties) can be used with success as a polymeric graft in the claimed composition which meet the minimum $T_g$ requirement.

The molecular weight of the graft polymeric moiety C is preferably sufficient to result in the formation of a "phase-separated" graft copolymer composition. Generally the molecular weight of the graft polymeric moiety will be within the range of from 2,000 to 60,000, and will preferably range from 2,000 to 13,000.

The macromer D also forms polymeric sidechains on the graft copolymer. The macromer D contains hydrophilic repeat units.

The macromer may be represented by the formula X—(Y)$_p$—Z—R. X is as defined above and is a moiety copolymerizable with monomers A and B or, in the alternative, capable of attachment to polymerized monomers A and B, Y is a divalent linking group, Z is a homo- or copolymeric moiety essentially unreactive at copolymerization conditions which contains hydrophilic repeat units, R is a terminal group, and p is 0 or 1.

A preferred Y divalent linking group is

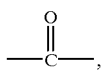

or a linking group which incorporates such a moiety.

Additional Y linking groups which may be employed in connection with the present invention include but are not limited to the following moieties:

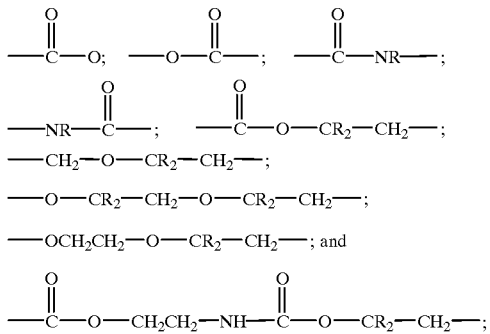

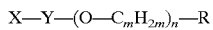

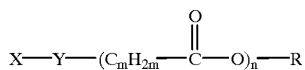

where R is hydrogen, alkyl or phenyl. Obviously, the presence of the Y linking group is optional in the event the moiety includes a functionality which enables the Z moiety to react with the X moiety. As the incorporation of macromolecular moieties in copolymers is well understood by those skilled in the art, the choice of a suitable X and Y moiety for use in the present invention may be readily made upon practice of the present invention. See, for example, the discussion in U.S. Pat. Nos. 3,786,116; 3,832,423; 3,842,058; 3,842,059; 3,842,146; and 4,554,324, herein incorporated by reference.

The Z moiety is preferably selected from the group consisting of (but not limited to) a polypropylene or polyethylene oxide radical, a polyethyloxazoline radical such as a radical of poly(2-ethyl-2-oxazoline), polyacrylic acid radical, polyvinyl alcohol radical, polyvinylpyrrolidone radical, polyvinyl caprolactam radical, polymethylvinyl ether radical or mixtures thereof. Exemplary D macromers formed from such radicals include but are not limited to ethoxylated or propoxylated hydroxy($C_{1-5}$)alkyl meth (acrylate)polymethylvinyl ether mono(meth)acrylate and beta-carboxyethyl acrylate. The molecular weight of the macromer used in the present invention is not critical but will generally range from about 300 to about 50,000, and preferably from about 300 to 3,000.

The Z moiety is preferably comprised solely of one or more hydrophilic monomer radicals. However, the Z moiety may also be a copolymer of hydrophilic and hydrophobic monomers. Desirably, any non-hydrophilic portion employed in such a Z copolymer is present in an amount of less than 50 percent by weight based on the weight of the macromer, and preferably less than 30 percent by weight.

The macromer D is preferably represented by the formula:

$$X-Y-(O-C_mH_{2m})_n-R$$

or $$X-Y-(C_mH_{2m}-\overset{O}{\underset{\|}{C}}-O)_n-R$$

wherein X and Y are as defined above and R represents a terminal group; and in which m is an integer of from 2 to 6 and n is an integer of up to 300. More specifically, macromer D may be an ethoxylated or propoxylated hydroxy($C_{1-5}$) alkyl (meth)acrylate represented by the formula:

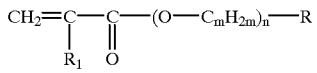

wherein $R_1$ is hydrogen or $C_{1-5}$ alkyl and R is terminal group. Preferably, m is 2 or 3 and n is 5 to 30, and R is OH, $C_{1-5}$ alkyl or nonyl-phenol.

Alternatively, macromer D may advantageously comprise a 2-carboxy ($C_{1-5}$)alkyl acrylate of the formula:

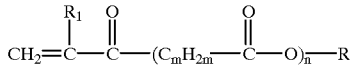

wherein $R_1$ is hydrogen or $C_{1-5}$ alkyl and R is a terminal group. Preferably, m is 2 or 3 and n is 4 to 30, and R is H, OH, $C_{1-5}$ alkyl or nonyl-phenol.

Of course, macromer D may incorporate mixtures of polyether and polyester repeat units with advantage which ratios are non-critical to practice of the present invention.

The macromer D may employ a variety of terminal groups R. While the terminal group may typically be OH or $C_{1-5}$ alkyl, it may be desirable to select a terminal group based on the functional character of the terminal group. For instance, suitable terminal groups include but are not limited to (1) acid/ionic groups such as carboxyl, phosphate or sulfate groups, (2) hydrophobic groups such as lower alkyl, phenyl or substituted phenyl, and (3) hydrophilic groups such as hydroxyl or amine groups.

Depending upon the terminal group employed, ionic end groups may be used to provide pH-dependent solubility characteristics for the copolymer. Hydrophobic terminal groups may be used to reduce the water solubility of the copolymer.

Other physical properties or characteristics of the copolymer may be modified by selection of suitable terminal groups. The copolymer of the present invention may be covalently or ionically-crosslinked in a conventional manner. Ionic terminal groups may be used to provide a desired degree of crosslinking; for example, by neutralizing acid moieties with metal hydroxides. High temperature performance may be enhanced by incorporating an acid functionality in conjunction with a ditertiary amine. Aqueous solution viscosities may be influenced by the presence of ionic terminal groups.

Preferably, the A monomer is present in the graft copolymer an amount of from 20 to 80 percent by weight, the B monomer is present in an amount of from 3 to 30 percent by weight, the optional C macromer is present in an amount of from 2 to 15 percent by weight, and the D macromer is present in an amount of from 5 to 60 percent by weight, based on the total weight of the respective components A, B, C, and D in the copolymer.

As noted above, the copolymer composition of the present invention may be prepared by any conventional polymerization technique, including (1) free radical-initiated copolymerization of components A and D and optionally B and C in the presence of a solvent, or (2) attachment of the macromer grafts to a preformed backbone polymer formed from copolymerized monomer A copolymerized with monomer B via reaction with a suitable functional group on the backbone polymer subsequent to formation of same.

Suitable copolymerization temperatures range from about 20° C. to about 150° C. for periods of time of from 2 to 24 hours until the desired degree of conversion occurs. Upon completion of the copolymerization process, the solvent is removed and a tacky copolymer results having acceptable adhesive properties. If desired, a suitable crosslinking agent may be employed to increase the molecular weight of the adhesive if desired.

The composition of the present invention successfully overcomes the deficiencies of prior art transdermal adhesives in several ways. The inclusion of an N-vinyl lactam monomer as a B monomer reduces the tendency of any pharmacologically active agent susceptible to crystallization (such as estrogen and/or progestin) present in the drug delivery system to crystallize within the system. This permits the active agent to remain effective over the entire period of time of delivery to the patient through the drug delivery device. The presence of the graft moieties enhances the ability of the adhesive system to retain its structural integrity and adhesive character during the period of use of the drug delivery device. More specifically, the presence of a graft macromeric moiety containing hydrophilic repeat units enhances the compatibility of any drug flux enhancer with the graft copolymer.

The pharmacologically active agent to be administered by use of the transdermal drug delivery means is employed in a conventional manner. Suitable active agents include those that are compatible with the administration system of the present invention and exhibit the expected benefit upon percutaneous administration. Such active agents include, without limitation, antibiotics, antipyretics, analgesics, anti-inflammatory drugs, antihistaminics, psychotropic drugs, coronary vasodilators, antiarrhythmics, antihypertensives, chemotherapeutic drugs, anticancer agents, antiemetics, vitamins, antispasmodics, antitussives, antifungal drugs, steroids, etc. Exemplary of the most commonly transdermally-administered active agents are clonidine, estrodiol, nicotine, nitroglycerine and scopolamine, each commercially available in transdermal devices. See U.S. Pat. No. 5,372,819, herein incorporated by reference, for a more detailed discussion of suitable percutaneous administered active agents.

In a preferred embodiment, estrogen and progestin may be administered by means of the present invention. The estrogen component may be either a synthetic or natural estrogen. Exemplary estrogen compounds include ethinyl estradiol, 17B estradiol, mestranol, estradiol valerate, 11-nitrato estradiol, 7-alpha-methyl-11-nitrato-estradiol, piperazine estrone sulfate, quinestranol and pharmaceutiically acceptable derivatives thereof. Exemplary progestin components include progesterone, 17-hydroxyprogesterone, dihydroprogesterone, medroxyprogesterone acetate, norethindrone, norethindrone acetate, norethynodrel, ethynodioldiacetate, norgestrel, levo-norgestrel, gestodene, delta-15-levonorgestrel, norgestimate, 17-deacetyl norgestimate, nomegesterol, nesterone, desogestrel, and 3-keto-deogestrel.

The use of a graft copolymer as a transdermal adhesive matrix is taught by U.S. Pat. No. 4,482,534. However, this patent is directed to a nitroglycerin adhesive preparation. The adhesive preparation disclosed in this patent may comprise a graft vinylpyrrolidone copolymer, either crosslinked or non-crosslinked. PCT publication WO 96/08229 also discloses a transdermal adhesive matrix comprised of a graft copolymer which may be used in association with estradiol or progestin. However, the disclosed adhesive does not achieve the balance of properties achieved by the present invention.

The adhesive may be used with particular advantage in association with a percutaneous penetration enhancer in a transdermal drug delivery device. Percutaneous penetration enhancers have the ability to increase permeability of skin to transdermally-administered pharmacologically active agents. Such enhancers are well-known in the art, and are discussed at length in U.S. Pat. Nos. 5,059,426 and 5,175,052, each herein incorporated by reference. By way of brief summary, such enhancers include but are not limited to surfactants (anionic, nonionic, cationic, zwitterionic), lipophilic solvents (terpenes, lactams), hydrophilic solvents (polyols, fatty acid esters, alcohols, sulfoxides), etc. Preferably, such enhancers are selected from the group consisting of sorbitols, ethoxylated alkyl phenols, glycerol, propylene glycol, polyethylene glycols, fatty acid esters, alcohols, and amines, and may be either water-soluble or non-water soluble (i.e. oily).

It has been found that the pressure sensitive adhesive of the present invention can be used with advantage upon admixture of percutaneous penetration enhancers with the base polymer to form a drug flux enhancer-tolerant pressure sensitive adhesive composition. That is, both oily or water-soluble percutaneous penetration enhancers can be admixed with the base polymer to maximize the ability of an incorporated pharmacologically active agent to be absorbed into the skin without adversely affecting the adhesive properties of the adhesive. Advantageously, it has been found that the percutaneous penetration enhancer can be used in amounts up to about 40 percent by weight, based on the weight of the composition, without adversely affecting the physical integrity of the adhesive or its adhesive properties. Such advantages can be attained irrespective of whether the percutaneous penetration enhancer is either oil or water-soluble which result is not well-attained by conventional adhesives. Preferably, the enhancer will be employed in an amount within the range of from 5 to 30 percent by weight, based on the weight of the composition.

The adhesive of the present invention may be used with advantage in a variety of conventional transdermal drug delivery devices. Such devices may take many forms. Generally, such devices comprise a backing material and an adhesive layer on at least a portion of the backing material. A release liner covers the adhesive layer until use at which time the liner is removed and the adhesive layer placed on the skin. The backing material is impermeable to the pharmacologically active agent. The pharmacologically active agent may be contained in either a liquid reservoir within the backing layer, within a matrix layer on said backing layer disposed between the adhesive layer and the backing layer, or within a layer of the drug flux enhancer-adhesive composition of the present invention. The manner of formulation of such various transdermal drug delivery systems is within the ability of one skilled in the art.

The pharmacologically active agent, in homogenous admixture with the pressure sensitive graft copolymer, is present optionally in an amount effective to provide the desired dosage to the patient. Generally, the active agent will be present in in an amount within the range of from 0.5 to 30 percent by weight, based on the total weight of the composition. One skilled in the art can readily determine the amount of pharmacologically active agent to employ in association with the graft copolymer to achieve the desired degree of administration.

In order to demonstrate the advantageous properties of the adhesive compositions of the present invention, various polymeric adhesive compositions were prepared having the compositions described in the following Examples.

EXAMPLE 1

A reaction mixture was prepared and 0.11 wt. % BPO was used as the catalyst. 30% of the mixture was charged to a 1-liter reaction vessel. Under a nitrogen atmosphere, the batch was heated to 72° C. over 15 minutes. After the initial 15 minutes, the remaining 70% of monomer/solvent mixture was added over 4 hours, maintaining a batch temperature of 71.5–74° C. Upon completion of the addition, the reactants were polymerized for 1 additional hour to produce a tackifier-free pressure sensitive adhesive. The reactor feed mix consisted of the following components:

| Monomers | Amount |
| --- | --- |
| Polystyrene methacrylate (macromer) | 21.00 grams |
| Ethoxylated nonyl-phenol acrylate (macromer) | 25.84 |
| Isooctyl acrylate (A monomer) | 56.52 |
| Hydroxy ethyl acrylate (B monomer) | 64.60 |
| Isobornyl acrylate (A monomer) | 25.84 |
| Lauryl acrylate (A monomer) | 96.90 |
| Stearyl acrylate (A monomer) | 32.30 |

| Solvents | Amount (Grams) |
| --- | --- |
| Ethyl acetate | 474.30 grams |
| Toluene | 52.70 |

EXAMPLE 2

The procedure of Example 1 was repeated using the following reactor feed components to produce a tackifier-free pressure sensitive adhesive with the exception that the reactants were added over 3.5 hours with a subsequent 1.5 hour reaction time:

| Monomers | Amount |
| --- | --- |
| Polystyrene methacrylate (macromer) | 23.20 grams |
| Ethoxylated nonyl-phenol acrylate (macromer) | 83.90 |
| Hydroxyl ethyl acrylate (B monomer) | 71.40 |
| Lauryl acrylate (A monomer) | 133.88 |
| Stearyl acrylate (A monomer) | 44.62 |

| Solvents | Amount |
| --- | --- |
| Ethyl acetate | 330.31 grams |
| Toluene | 147.90 |
| Isopropyl alcohol | 14.79 |

EXAMPLE 3

The procedure of Example 1 was repeated using the following reactor feed components to produce a tackifier-free pressure sensitive adhesive with the exception that the reactants were added over 3.5 hours with a subsequent 1.5 hour reaction time:

| Monomers | Amount (wt. %) |
| --- | --- |
| Polystyrene methacrylate (macromer) | 23.21 grams |
| Ethoxylated nonyl-phenol acrylate (macromer) | 71.40 |
| Hydroxyl ethyl acrylate (B monomer) | 85.68 |
| Lauryl acrylate (A monomer) | 107.09 |
| Stearyl acrylate (A monomer) | 33.92 |
| Isobornyl acrylate (A monomer) | 35.70 |

| Solvents | Amount |
| --- | --- |
| Ethyl acetate | 330.31 grams |
| Toluene | 147.90 |
| Isopropyl alcohol | 14.79 |

EXAMPLE 4

The procedure of Example 1 was repeated using the following reactor feed components to produce a tackifier-free pressure sensitive adhesive, with the exception that the reactants were added over 3.5 hours with a subsequent 1.5 hour reaction time:

| Monomers | Amount |
| --- | --- |
| Tridecyl acrylate (A monomer) | 178.50 grams |
| Ethoxylated nonyl-phenol acrylate (macromer) | 76.76 |
| Hydroxyl ethyl acrylate (B monomer) | 71.40 |
| Polystyrene methacrylate (macromer) | 30.34 |

| Solvents | Amount |
| --- | --- |
| Ethyl acetate | 330.31 grams |
| Isopropyl alcohol | 14.79 |
| Toluene | 147.90 |

What is claimed is:

1. A pressure sensitive adhesive drug delivery composition for use in the transdermal administration of a pharmacologically active agent comprised of a homogeneous admixture of a hydrophilic macromer reinforced copolymer and a pharmacologically active agent, said copolymer comprising the crosslinked reaction product of:
   (1) at least one A monomer consisting of a monomeric (meth)acrylic acid ester of a non-tertiary alcohol, said alcohol having from 1 to 30 carbon atoms, wherein at least about 30 percent by weight of said A monomer consists of a monomeric (meth)acrylic acid ester of a non-tertiary alcohol having at least 12 carbon atoms, and said at least one A monomer exhibiting an average number of carbon atoms in the alcohol portion of the total (meth)acrylic acid esters of at least 10,
   (2) optionally at least one B monomer,
   (3) optionally a polymeric graft moiety C having a $T_g$ greater than 20° C., and
   (4) a graft macromer D containing hydrophilic repeat units.

2. The composition of claim 1 wherein said graft moiety C is a polymerized monoalkenyl-substituted aromatic hydrocarbon.

3. The composition of claim 2 wherein said polymerized monoalkenyl-substituted aromatic hydrocarbon comprises polystyrene.

4. The composition of claim 1 wherein said at least one A monomer comprises an ester of (meth)acrylic acid with a non-tertiary alcohol selected from the group consisting of 1-butanol, 1-pentanol, 2-pentanol, 3-pentanol, 2-methyl-1-butanol, 1-methyl-1-pentanol, 2-methyl-1-pentanol, 3-methyl-1-pentanol, 2-ethyl-1-butanol, 3,5,5-trimethyl-1-hexanol, 3-heptanol, 2-octanol, 1-decanol, and 1-dodecanol.

5. The composition of claim 1 wherein the A monomer is present in the copolymer in an amount within the range of from about 20 to 80 percent by weight.

6. The composition of claim 1 wherein the B monomer is present in the copolymer in an amount within the range of from about 3 to 30 percent by weight.

7. The composition of claim 1 wherein the D macromer is present in the copolymer in an amount within the range of from about 5 to 60 percent by weight.

8. The composition of claim 1 wherein a B monomer is present selected from the group consisting of hydroxy($C_{1-5}$) alkyl acrylates, hydroxy($C_{1-5}$)alkyl methacrylates, dihydroxy($C_{1-5}$)alkyl acrylates, dihydroxy($C_{1-5}$)alkyl methacrylates and mixtures thereof.

9. The composition of claim 1 wherein said B monomer is selected from the group consisting of acrylamide, methacrylamide, N-methylacrylamide, N-ethylacrylamide, N-methylolacrylamide, N-hydroxyethylacrylamide, diacetone acrylamide, N,N-dimethylacrylamide, N,N-diethylacrylamide, N-ethyl-N-aminoethyl acrylamide, N-ethyl-N-hydroxyethylacrylamide, N,N-dimethylolacrylamide, N,N-dihydroxyethylacrylamide and mixtures thereof.

10. The composition of claim 1 wherein said macromer D is defined by the formula X—$(Y)_p$—Z—R, wherein X is a moiety copolymerizable with monomers A and B or capable of attachment to copolymerized monomers A and B, Y is a divalent linking group, Z is a homo- or copolymeric moiety containing hydrophilic repeat units, R is a terminal group, and p is 0 or 1.

11. The composition of claim 10 wherein Z is selected from the group consisting of a polyalkylene oxide radical, a polyethyloxazoline radical, a polyacrylic acid radical, a polyvinyl alcohol radical, a polyvinylpyrrolidone radical, a polyvinylcaprolactam radical and a polymethylvinyl ether radical.

12. The composition of claim 1 wherein said macromer D is defined by the formula:

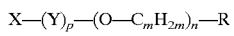

wherein X is a moiety copolymerizable with monomers A and B or capable of attachment to copolymerized monomers A and B, Y is a divalent linking group, R is a terminal group, m is an integer of from 2 to 6, n is an integer of from 5 to 300, and p is 0 or 1.

13. The composition of claim 12 wherein said macromer D is defined by the formula

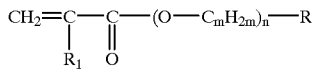

wherein $R_1$ is hydrogen or $C_{1-5}$ alkyl, R is a terminal group, and n is an integer from 5 to 30.

14. The composition of claim 1 wherein said A monomer comprises a monomeric (meth)acrylic acid ester of a non-tertiary alcohol which has from 12 to 18 carbon atoms.

15. The composition of claim 1 wherein said macromer D is selected from the group consisting of ethoxylated and propoxylated hydroxy ($C_{1-5}$ alkyl) (meth)acrylate, poly(2-ethyl-2-oxazoline), polyacrylic acid, polyvinyl alcohol, polyvinyl pyrrolidone, polyvinyl caprolactam and polymethylvinyl ether mono(meth)acrylate.

16. The composition of claim 1 wherein a B monomer is present comprising an N-vinyl lactam monomer selected from the group consisting of N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, N-vinyl-2-caprolactam, and mixtures thereof.

17. The composition of claim 1 wherein said copolymer comprises the reaction product of at least one A monomer, at least one N-vinyl lactam B monomer, at least one polymeric graft moiety C and a graft macromer D.

18. The composition of claim 1 or 17 wherein said pharmacologically active agent is selected from the group consisting of estrogen, progestin and mixtures thereof.

19. The composition of claim 1 wherein said macromer D is 2-carboxy($C_{1-5}$)alkyl acrylate.

20. The composition of claim 1 wherein said macromer D is defined by the formula:

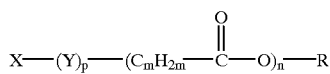

wherein X is a moiety copolymerizable with monomers A and B or capable of attachment to copolymerized monomers A and B, Y is a divalent linking group, R is a terminal group, m is an integer of from 2 to 6, n is an integer of up to 300, and p is 0 or 1.

21. The composition of claim 20 wherein said macromer D is defined by the formula:

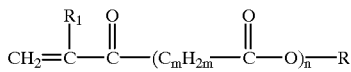

wherein $R_1$ is hydrogen or $C_{1-5}$ alkyl, m is 2 or 3, n is 4 to 30, and R is H, OH, $C_{1-5}$ alkyl or nonyl-phenol.

22. The composition of claim 20 wherein R is OH, $C_{1-5}$ alkyl, or nonyl-phenol.

23. The composition of claim 20 wherein n is an integer of from 4 to 30.

24. A transdermal delivery system for administering a pharmacologically active agent comprising a flexible backing material impermeable to said active agent and a pressure sensitive adhesive layer on at least a portion of said backing material for adhesion of said transdermal delivery system to the skin, said pressure sensitive adhesive being in homogeneous admixture with said active agent, said pressure sensitive adhesive comprising a crosslinked graft macromer reinforced copolymer formed by the reaction of:

(1) at least one A monomer consisting of a monomeric (meth)acrylic acid ester of a non-tertiary alcohol, said alcohol having from 1 to 30 carbon atoms, wherein at least about 30 percent by weight of said A monomer consists of a monomeric (meth)acrylic acid ester of a non-tertiary alcohol having at least 12 carbon atoms, and said at least one A monomer exhibiting an average number of carbon atoms in the alcohol portion of the total (meth)acrylic acid esters of at least 10, (2) optionally at least one B monomer, (3) optionally a polymeric graft moiety C having a $T_g$ greater than 20° C., and (4) a graft macromer D containing hydrophilic repeat units.

25. The delivery system of claim 24 wherein said graft moiety C is a polymerized monoalkenyl-substituted aromatic hydrocarbon.

26. The delivery system of claim 25 wherein said polymerized monoalkenyl-substituted aromatic hydrocarbon comprises polystyrene.

27. The delivery system of claim 24 wherein said at least one A monomer comprises an ester of (meth)acrylic acid with a non-tertiary alcohol selected from the group consisting of 1-butanol, 1-pentanol, 2-pentanol, 3-pentanol, 2-methyl-1-butanol, 1-methyl-1-pentanol, 2-imethyl-1-pentanol, 3-methyl-1-pentanol, 2-ethyl-1-butanol, 3,5,5-trimethyl-1-hexanol, 3-heptanol, 2-octanol, 1-decanol, and 1-dodecanol.

28. The delivery system of claim 24 wherein the A monomer is present in the copolymer in an amount within the range of from about 20 to 80 percent by weight.

29. The delivery system of claim 24 wherein a B monomer is present in the copolymer in an amount within the range of from about 3 to 30 percent by weight.

30. The delivery system of claim 24 wherein the D macromer is present in the copolymer in an amount within the range of from about 5 to 60 percent by weight.

31. The delivery system of claim 24 wherein a B monomer is present selected from the group consisting of hydroxy($C_{1-5}$)alkyl acrylates, hydroxy($C_{1-5}$)alkyl methacrylates, dihydroxy($C_{1-5}$)alkyl acrylates, dihydroxy($C_{1-5}$)alkyl methacrylates and mixtures thereof.

32. The composition of claim 24 wherein said B monomer is selected from the group consisting of acrylamide, methacrylamide, N-methylacrylamide, N-ethylacrylamide, N-methylolacrylamide, N-hydroxyethylacrylamide, diacetone acrylamide, N,N-dimethylacrylamide, N,N-diethylacrylamide, N-ethyl-N-aminoethyl acrylamide, N-ethyl-N-hydroxyethylacrylamide, N,N-dimethylolacrylamide, N,N-dihydroxyethylacrylamide and mixtures thereof.

33. The delivery system of claim 24 wherein said macromer D is defined by the formula X—$(Y)_p$—Z—R, wherein X is a moiety copolymerizable with monomers A and B or capable of attachment to copolymerized monomers A and B, Y is a divalent linking group, Z is a homo- or copolymeric moiety containing hydrophilic repeat units, R is a terminal group, and p is 0 or 1.

34. The delivery system of claim 33 wherein Z is selected from the group consisting of a polyalkylene oxide radical, a polyethyloxazoline radical, a polyacrylic acid radical, a polyvinyl alcohol radical, a polyvinylpyrrolidone radical, a polyvinylcaprolactam radical and a polymethylvinyl ether radical.

35. The delivery system of claim 24 wherein said macromer D is defined by the formula:

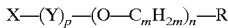

wherein X is a moiety copolymerizable with monomers A and B or capable of attachment to copolymerized monomers A and B, Y is a divalent linking group, R is a terminal group, m is an integer of from 2 to 6, n is an integer of up to 300, and p is 0 or 1.

36. The delivery system of claim 35 wherein said macromer D is defined by the formula

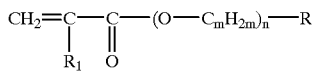

wherein $R_1$ is hydrogen or $C_{1-5}$ alkyl, R is a terminal group, and n is an integer from 5 to 30.

37. The delivery system of claim 24 wherein said A monomer comprises a monomeric (meth)acrylic acid ester of a non-tertiary alcohol which has from 12 to 18 carbon atoms.

38. The delivery system of claim 24 wherein said macromer D is selected from the group consisting of ethoxylated and propoxylated hydroxy ($C_{1-5}$ alkyl) (meth)acrylate, poly (2-ethyl-2-oxazoline), polyacrylic acid, polyvinyl alcohol, polyvinyl pyrrolidone, polyvinyl caprolactam and polymethylvinyl ether mono(meth)acrylate.

39. The delivery system of claim 24 wherein a B monomer is present comprising an N-vinyl lactam monomer selected from the group consisting of N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, N-vinyl-2-caprolactam, and mixtures thereof.

40. The delivery system of claim 24 wherein said copolymer comprises the reaction product of at least one A monomer, at least one N-vinyl lactam B monomer, at least one polymeric graft moiety C and a water-soluble or water-dispersible macromer D.

41. The delivery system of claim 24 or 40 wherein said pharmacologically active agent is selected from the group consisting of estrogen, progestin and mixtures thereof.

42. The delivery system of claim 24 wherein said macromer D is 2-carboxy($C_{1-5}$)alkyl acrylate.

43. The delivery system of claim 24 wherein said macromer D is defined by the formula:

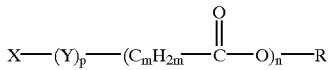

wherein X is a moiety copolymerizable with monomers A and B or capable of attachment to copolymerized monomers A and B, Y is a divalent linking group, R is a terminal group, m is an integer of from 2 to 6, n is an integer of up to 300, and p is 0 or 1.

44. The delivery system of claim 43 wherein said macromer D is defined by the formula:

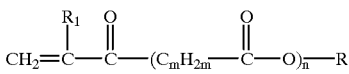

wherein $R_1$ is hydrogen or $C_{1-5}$ alkyl, m is 2 or 3, n is 4 to 30, and R is H, OH, $C_{1-5}$ alkyl or nonyl-phenol.

45. The delivery system of claim 43 wherein R is OH, $C_{1-5}$ alkyl or nonyl-phenol.

46. The delivery system of claim 43 wherein n is an integer of from 4 to 30.

47. In a transdermal delivery system for administering a pharmacologically active agent comprising a flexible backing material and a pressure sensitive adhesive layer for adhesion of said transdermal delivery system to the skin, said pharmacologically active agent being contained within either a reservoir attached to said backing material or within a matrix layer between said backing material and said pressure sensitive adhesive layer, the improvement wherein said pressure sensitive adhesive comprises an optionally crosslinked graft macromer reinforced copolymer formed by the reaction of:

(1) at least one A monomer consisting of a monomeric (meth)acrylic acid ester of a non-tertiary alcohol, said alcohol having from 1 to 30 carbon atoms, wherein at least about 30 percent by weight of said A monomer consists of a monomeric (meth)acrylic acid ester of a non-tertiary alcohol having at least 12 carbon atoms, and said at least one A monomer exhibiting an average number of carbon atoms in the alcohol portion of the total (meth)acrylic acid esters of at least 10, (2) optionally at least one B monomer, (3) optionally a polymeric graft moiety C having a $T_g$ greater than 20° C., and (4) a graft macromer D containing hydrophilic repeat units.

48. The delivery system of claim 47 wherein said graft moiety C is a polymerized monoalkenyl-substituted aromatic hydrocarbon.

49. The delivery system of claim 48 wherein said polymerized monoalkenyl-substituted aromatic hydrocarbon comprises polystyrene.

50. The delivery system of claim 47 wherein said at least one A monomer comprises an ester of (meth)acrylic acid with a non-tertiary alcohol selected from the group consisting of 1-butanol, 1-pentanol, 2-pentanol, 3-pentanol, 2-methyl-1-butanol, 1-methyl-1-pentanol, 2-methyl-1-pentanol, 3-methyl-1-pentanol, 2-ethyl-1-butanol, 3,5,5-trimethyl-1-hexanol, 3-heptanol, 2-octanol, 1-decanol, and 1-dodecanol.

51. The delivery system of claim 47 wherein the A monomer is present in the copolymer in an amount within the range of from about 20 to 80 percent by weight.

52. The delivery system of claim 47 wherein a B monomer is present in the copolymer in an amount within the range of from about 3 to 30 percent by weight.

53. The delivery system of claim 47 wherein the D macromer is present in the copolymer in an amount within the range of from about 5 to 60 percent by weight.

54. The delivery system of claim 47 wherein a B monomer is present selected from the group consisting of hydroxy $(C_{1-5})$alkyl acrylates, hydroxy$(C_{1-5})$alkyl methacrylates, dihydroxy$(C_{1-5})$alkyl acrylates, dihydroxy$(C_{1-5})$alkyl methacrylates and mixtures thereof.

55. The composition of claim 47 wherein said B monomer is selected from the group consisting of acrylamide, methacrylamide, N-methylacrylamide, N-ethylacrylamide, N-methylolacrylamide, N-hydroxyethylacrylanide, diacetone acrylamide, N,N-dimethylacrylamide, N,N-diethylacrylamide, N-ethyl-N-aminoethyl acrylamide, N-ethyl-N-hydroxyethylacrylamide, N,N-dimethylolacrylamide, N,N-dihydroxyethylacrylamide and mixtures thereof.

56. The delivery system of claim 47 wherein said macromer D is defined by the formula X—$(Y)_p$—Z—R, wherein X is a moiety copolymerizable with monomers A and B or capable of attachment to copolymerized monomers A and B, Y is a divalent linking group, Z is a homo- or copolymeric moiety containing hydrophilic repeat units, R is a terminal group, and p is 0 or 1.

57. The delivery system of claim 56 wherein Z is selected from the group consisting of a polyalkylene oxide radical, a polyethyloxazoline radical, a polyacrylic acid radical, a polyvinyl alcohol radical, a polyvinylpyrrolidone radical, a polyvinylcaprolactam radical and a polymethylvinyl ether radical.

58. The delivery system of claim 47 wherein said macromer D is defined by the formula:

X—$(Y)_p$—(O—$C_mH_{2m}$)$_n$—R wherein X is a moiety copolymerizable with monomers A and B or capable of attachment to copolymerized monomers A and B, Y is a divalent linking group, R is a terminal group, m is an integer of from 2 to 6, n is an integer of up to 300, and p is 0 or 1.

59. The delivery system of claim 58 wherein said macromer D is defined by the formula

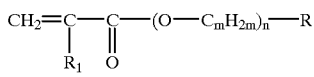

wherein $R_1$ is hydrogen or $C_{1-5}$ alkyl, R is a terminal group, and n is an integer from 5 to 30.

60. The delivery system of claim 47 wherein said A monomer comprises a monomeric (meth)acrylic acid ester of a non-tertiary alcohol which has from 12 to 18 carbon atoms.

61. The delivery system of claim 47 wherein said macromer D is selected from the group consisting of ethoxylated and propoxylated hydroxy ($C_{1-5}$ alkyl) (meth)acrylate, poly (2-ethyl-2-oxazoline), polyacrylic acid, polyvinyl alcohol, polyvinyl pyrrolidone, polyvinyl caprolactam and polymethylvinyl ether mono(meth)acrylate.

62. The delivery system of claim 47 wherein a B monomer is present comprising an N-vinyl lactam monomer selected from the group consisting of N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, N-vinyl-2-caprolactam, and mixtures thereof.

63. The delivery system of claim 47 wherein said copolymer comprises the reaction product of at least one A monomer, at least one N-vinyl lactam B monomer, at least one polymeric graft moiety C and a water-soluble or water-dispersible macromer D.

64. The delivery system of claim 63 wherein said pharmacologically active agent is selected from the group consisting of estrogen, progestin and mixtures thereof.

65. The delivery system of claim 47 wherein said macromer D is 2-carboxy$(C_{1-5})$alkyl acrylate.

66. The delivery system of claim 47 wherein said macromer D is defined by the formula:

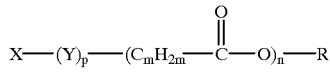

wherein X is a moiety copolymerizable with monomers A and B or capable of attachment to copolymerized monomers A and B, Y is a divalent linking group, R is a terminal group, m is an integer of from 2 to 6, n is an integer of up to 300, and p is 0 or 1.

67. The delivery system of claim 66 wherein said macromer D is defined by the formula:

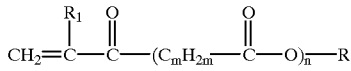

wherein $R_1$ is hydrogen or $C_{1-5}$ alkyl, m is 2 or 3, n is 4 to 30, and R is H, OH, $C_{1-5}$ alkyl or nonyl-phenol.

68. The delivery system of claim 66 wherein R is OH, $C_{1-5}$ alkyl or nonyl-phenol.

69. The delivery system of claim 66 wherein n is an integer of from 4 to 30.

70. The delivery system of any one of claims 24–32 wherein a percutaneous penetration enhancer is present in said admixture.

71. The composition of any one of claims 1–9 wherein a percutaneous penetration enhancer is present in said admixture.

72. The delivery system of any one of claims 47–55 wherein a percutaneous penetration enhancer is present in admixture with said pressure sensitive adhesive.

73. A pressure sensitive adhesive composition for use in the transdermal administration of a pharmacologically active agent comprised of an admixture of a hydrophilic macromer reinforced copolymer, a percutaneous penetration enhancer and a pharmacologically active agent, said copolymer comprising the reaction product of:
   (1) at least one A monomer consisting of a monomeric (meth)acrylic acid ester of a non-tertiary alcohol, said alcohol having from 1 to 30 carbon atoms, wherein at least about 30 percent by weight of said A monomer consists of a monomeric (meth)acrylic acid ester of a non-tertiary alcohol having at least 12 carbon atoms, and said at least one A monomer exhibiting an average number of carbon atoms in the alcohol portion of the total (meth)acrylic acid esters of at least 10,
   (2) optionally at least one B monomer,
   (3) optionally a polymeric graft moiety C having a $T_g$ greater than 20° C., and
   (4) a graft macromer D containing hydrophilic repeat units.

74. The composition of claim 73 wherein a polymeric graft moiety C is present.

75. The composition of claim 74 wherein a graft moiety C is present comprising a polymerized monoalkenyl-substituted aromatic hydrocarbon.

76. The composition of claim 74 wherein said polymerized monoalkenyl-substituted aromatic hydrocarbon comprises polystyrene.

77. The composition of claim 73 wherein said at least one A monomer comprises an ester of (meth)acrylic acid with a non-tertiary alcohol selected from the group consisting of 1-butanol, 1-pentanol, 2-pentanol, 3-pentanol, 2-methyl-1-butanol, 1-methyl-1-pentanol, 2-methyl-1-pentanol, 3-methyl-1-pentanol, 2-ethyl-1-butanol, 3,5,5-trimethyl-1-hexanol, 3-heptanol, 2-octanol, 1-decanol, and 1-dodecanol.

78. The composition of claim 73 wherein said A monomer comprises a (meth)acrylic acid ester of a non-tertiary alcohol which has from 12 to 18 carbon atoms.

79. The composition of claim 73 wherein the A monomer is present in the copolymer in an amount within the range of from about 20 to 80 percent by weight.

80. The composition of claim 73 wherein a B monomer is present in the copolymer in an amount within the range of from about 3 to 30 percent by weight.

81. The composition of claim 73 wherein the D macromer is present in the copolymer in an amount within the range of from about 5 to 60 percent by weight.

82. The composition of claim 73 wherein a B monomer is present selected from the group consisting of hydroxy($C_{1-5}$) alkyl acrylates, hydroxy($C_{1-5}$)alkyl methacrylates, dihydroxy($C_{1-5}$)alkyl acrylates, dihydroxy($C_{1-5}$)alkyl methacrylates and mixtures thereof.

83. The composition of claim 73 wherein a B monomer is present selected from the group consisting of acrylamide, methacrylamide, N-methylacrylamide, N-ethylacrylamide, N-methylolacrylamide, N-hydroxyethylacrylamide, diacetone acrylamide, N,N-dimethylacrylamide, N,N-diethylacrylamide, N-ethyl-N-aminoethyl acrylamide, N-ethyl-N-hydroxyethylacrylamide, N,N-dimethylolacrylamide, N,N-dihydroxyethylacrylamide and mixtures thereof.

84. The composition of claim 73 wherein a B monomer is present comprising an N-vinyl lactam monomer selected from the group consisting of N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, N-vinyl-2-caprolactam, and mixtures thereof.

85. The composition of claim 73 wherein said macromer D is defined by the formula X—(Y)$_p$—Z—R, wherein X is a moiety copolymerizable with monomers A and B or capable of attachment to copolymerized monomers A and B, Y is a divalent linking group, Z is a homo- or copolymeric moiety containing hydrophilic repeat units, R is a terminal group, and p is 0 or 1.

86. The composition of claim 85 wherein Z is selected from the group consisting of a polyalkylene oxide radical, a polyethyloxazoline radical, a polyacrylic acid radical, a polyvinyl alcohol radical, a polyvinylpyrrolidone radical, a polyvinylcaprolactam radical and a polymethylvinyl ether radical.

87. The composition of claim 85 wherein said macromer D is defined by the formula:

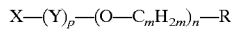

wherein X is a moiety copolymerizable with monomers A and B or capable of attachment to copolymerized monomers A and B, Y is a divalent linking group, R is a terminal group, m is an integer of from 2 to 6, n is an integer of up to 300, and p is 0 or 1.

88. The composition of claim 85 wherein said macromer D is defined by the formula

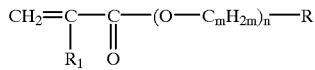

wherein $R_1$ is hydrogen or $C_{1-5}$ alkyl, R is a terminal group, and n is an integer from 5 to 30.

89. The composition of claim 85 wherein said macromer D is defined by the formula:

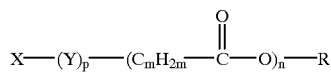

wherein X is a moiety copolymerizable with monomers A and B or capable of attachment to copolymerized monomers A and B, Y is a divalent linking group, R is a terminal group, m is an integer of from 2 to 6, n is an integer of up to 300, and p is 0 or 1.

90. The composition of claim 73 wherein said copolymer comprises the reaction product of at least one A monomer, at least one N-vinyl lactam B monomer, at least one polymeric graft moiety C and a graft macromer D.

91. The composition of claim 85 wherein said copolymer comprises the reaction product of at least one A monomer, at least one N-vinyl lactam B monomer, at least one polymeric graft moiety C and a graft macromer D.

92. The composition of claim 73 wherein said pharmacologically active agent is selected from the group consisting of estrogen, progestin and mixtures thereof.

93. The composition of claim 90 wherein said pharmacologically active agent is selected from the group consisting of estrogen, progestin and mixtures thereof.

94. The composition of claim 91 wherein said pharmacologically active agent is selected from the group consisting of estrogen, progestin and mixtures thereof.

95. A transdermal delivery system for administering a pharmacologically active agent comprising a flexible backing material impermeable to said active agent and a pressure sensitive adhesive layer on at least a portion of said backing layer in admixture with a percutaneous penetration enhancer and a pharmacologically active agent, said pressure sensitive adhesive comprising a graft macromer reinforced copolymer formed by the reaction of:
  (1) at least one A monomer consisting of a monomeric (meth)acrylic acid ester of a non-tertiary alcohol, said alcohol having from 1 to 30 carbon atoms, wherein at least about 30 percent by weight of said A monomer consists of a monomeric (meth)acrylic acid ester of a non-tertiary alcohol having at least 12 carbon atoms, and said at least one A monomer exhibiting an average number of carbon atoms in the alcohol portion of the total (meth)acrylic acid esters of at least 10,
  (2) optionally at least one B monomer,
  (3) optionally a polymeric graft moiety C having a $T_g$ greater than 20° C., and
  (4) a graft macromer D containing hydrophilic repeat units.

96. The delivery system of claim 95 wherein a polymeric graft moiety C is present.

97. The delivery system of claim 95 wherein said graft moiety C is a polymerized monoalkenyl-substituted aromatic hydrocarbon.

98. The delivery system of claim 95 wherein said polymerized monoalkenyl-substituted aromatic hydrocarbon comprises polystyrene.

99. The delivery system of claim 95 wherein said at least one A monomer comprises an ester of (meth)acrylic acid with a non-tertiary alcohol selected from the group consisting of 1-butanol, 1-pentanol, 2-pentanol, 3-pentanol, 2-methyl-1-butanol, 1-methyl-1-pentanol, 2-methyl-1-pentanol, 3-methyl-1-pentanol, 2-ethyl-1-butanol, 3,5,5-trimethyl-1-hexanol, 3-heptanol, 2-octanol, 1-decanol, and 1-dodecanol.

100. The delivery system of claim 95 wherein said A monomer comprises a (meth)acrylic acid ester of a non-tertiary alcohol which has from 12 to 18 carbon atoms.

101. The delivery system of claim 95 wherein the A monomer is present in the copolymer in an amount within the range of from about 20 to 80 percent by weight.

102. The delivery system of claim 95 wherein a B monomer is present in the copolymer in an amount within the range of from about 3 to 30 percent by weight.

103. The delivery system of claim 95 wherein the D macromer is present in the copolymer in an amount within the range of from about 5 to 60 percent by weight.

104. The delivery system of claim 95 wherein a B monomer is present selected from the group consisting of hydroxy($C_{1-5}$)alkyl acrylates, hydroxy($C_{1-5}$)alkyl methacrylates, dihydroxy($C_{1-5}$)alkyl acrylates, dihydroxy ($C_{1-5}$)alkyl methacrylates and mixtures thereof.

105. The composition of claim 95 wherein said B monomer is selected from the group consisting of acrylamide, methacrylamide, N-methylacrylamide, N-ethylacrylamide, N-methylolacrylamide, N-hydroxyethylacrylamide, diacetone acrylamide, N,N-dimethylacrylamide, N,N-diethylacrylamide, N-ethyl-N-aminoethyl acrylamide, N-ethyl-N-hydroxyethylacrylamide, N,N-dimethylolacrylamide, N,N-dihydroxyethylacrylamide and mixtures thereof.

106. The delivery system of claim 95 wherein a B monomer is present comprising an N-vinyl lactam monomer selected from the group consisting of N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, N-vinyl-2-caprolactam, and mixtures thereof.

107. The delivery system of claim 95 wherein said macromer D is defined by the formula X—$(Y)_p$—Z—R, wherein X is a moiety copolymerizable with monomers A and B or capable of attachment to copolymerized monomers A and B, Y is a divalent linking group, Z is a homo- or copolymeric moiety containing hydrophilic repeat units, R is a terminal group, and p is 0 or 1.

108. The delivery system of claim 107 wherein Z is selected from the group consisting of a polyalkylene oxide radical, a polyethyloxazoline radical, a polyacrylic acid radical, a polyvinyl alcohol radical, a polyvinylpyrrolidone radical, a polyvinylcaprolactam radical and a polymethylvinyl ether radical.

109. The delivery system of claim 107 wherein said macromer D is defined by the formula:

$$X\text{—}(Y)_p\text{—}(O\text{—}C_mH_{2m})_n\text{—}R$$

wherein X is a moiety copolymerizable with monomers A and B or capable of attachment to copolymerized monomers A and B, Y is a divalent linking group, R is a terminal group, m is an integer of from 2 to 6, n is an integer of up to 300, and p is 0 or 1.

110. The delivery system of claim 109 wherein said macromer D is defined by the formula $$CH_2\text{=}C\text{—}\underset{\underset{O}{\|}}{C}\text{—}(O\text{—}C_mH_{2m})_n\text{—}R$$
$$\ \ \ \ \ \ \ \ |$$
$$\ \ \ \ \ \ \ R_1$$

wherein $R_1$ is hydrogen or $C_{1-5}$alkyl, R is a terminal group, and n is an integer from 5 to 30.

111. The delivery system of claim 107 wherein said macromer D is defined by the formula:

$$X\text{—}(Y)_p\text{—}(C_mH_{2m}\text{—}\underset{\underset{}{}}{\overset{\overset{O}{\|}}{C}}\text{—}O)_n\text{—}R$$

wherein X is a moiety copolymerizable with monomers A and B or capable of attachment to copolymerized monomers A and B, Y is a divalent linking group, R is a terminal group, m is an integer of from 2 to 6, n is an integer of up to 300, and p is 0 or 1.

112. The delivery system of claim 95 wherein said copolymer comprises the reaction product of at least one A monomer, at least one N-vinyl lactam B monomer, at least one polymeric graft moiety C and a water-soluble or water-dispersible macromer D.

113. The delivery system of claim 107 wherein said copolymer comprises the reaction product of at least one A monomer, at least one N-vinyl lactam B monomer, at least one polymeric graft moiety C and a water-soluble or water-dispersible macromer D.

114. The delivery system of claim 95 wherein said pharmacologically active agent is selected from the group consisting of estrogen, progestin and mixtures thereof.

115. The delivery system of claim 112 wherein said pharmacologically active agent is selected from the group consisting of estrogen, progestin and mixtures thereof.

116. The delivery system of claims 113 wherein said pharmacologically active agent is selected from the group consisting of estrogen, progestin and mixtures thereof.

* * * * *